United States Patent
Rose et al.

(10) Patent No.: US 9,380,810 B2
(45) Date of Patent: Jul. 5, 2016

(54) TOBACCO-BASED NICOTINE AEROSOL GENERATION SYSTEM

(75) Inventors: Seth D. Rose, Tempe, AZ (US); James Edward Turner, Homewood, IL (US); Thangaraju Murugesan, Durham, NC (US); Jed E. Rose, Durham, NC (US)

(73) Assignee: Philip Morris Products S.A., Neuchatel (CH)

( * ) Notice: Subject to any disclaimer, the term of this patent is extended or adjusted under 35 U.S.C. 154(b) by 1102 days.

(21) Appl. No.: 13/256,816

(22) PCT Filed: Mar. 9, 2010

(86) PCT No.: PCT/US2010/026614
§ 371 (c)(1),
(2), (4) Date: Sep. 15, 2011

(87) PCT Pub. No.: WO2010/107613
PCT Pub. Date: Sep. 23, 2010

(65) Prior Publication Data
US 2012/0006342 A1    Jan. 12, 2012

Related U.S. Application Data

(60) Provisional application No. 61/160,904, filed on Mar. 17, 2009.

(51) Int. Cl.
*A24F 47/00* (2006.01)
*A61M 15/06* (2006.01)
*A61M 11/04* (2006.01)

(52) U.S. Cl.
CPC .............. *A24F 47/008* (2013.01); *A24F 47/002* (2013.01); *A24F 47/006* (2013.01);
(Continued)

(58) Field of Classification Search
CPC ..... A24F 47/00; A24F 47/002; A24F 47/006; A24F 47/008
See application file for complete search history.

(56) References Cited

U.S. PATENT DOCUMENTS

| 830,626 A | 9/1906 | Van Nes |
| 3,258,015 A | 6/1966 | Ellis et al. |

(Continued)

FOREIGN PATENT DOCUMENTS

| CN | 86102917 A | 11/1987 |
| EP | 0148749 A2 | 7/1985 |

(Continued)

OTHER PUBLICATIONS

Poon, Wilson, "Cigarette Smoke: Size Distribution and Effects on Filters", no date, American Filtration & Separations Society, http://www.afssociety.org/air-filtration/89-cigarette-smoke-size-distribution-and-effects-on-filters. See data cited from "Chung & Dunn-Rankin (1996)" which is listed in the reference as I. Ching and D. Dunn-Rankin (1996).*

(Continued)

*Primary Examiner* — Michael J Felton
(74) *Attorney, Agent, or Firm* — Mueting, Raasch & Gebhardt, P.A.

(57) ABSTRACT

The invention relates to devices and methods for delivering nicotine and/or other alkaloids from tobacco, other plants and other natural sources. More particularly, the invention relates to devices and methods for delivering an aerosol of nicotine to a user's lungs without combustion of the nicotine source materials.

30 Claims, 7 Drawing Sheets

(52) U.S. Cl.
CPC ........... *A61M11/042* (2014.02); *A61M 11/047* (2014.02); *A61M 15/06* (2013.01); *A61M 2206/14* (2013.01)

(56) References Cited

U.S. PATENT DOCUMENTS

| | | | |
|---|---|---|---|
| 3,356,094 | A | 12/1967 | Ellis et al. |
| 4,715,387 | A | 12/1987 | Rose |
| 4,765,348 | A | 8/1988 | Honeycutt |
| 4,776,353 | A | 10/1988 | Lilja et al. |
| 4,830,028 | A | 5/1989 | Lawson et al. |
| 4,836,224 | A | 6/1989 | Lawson et al. |
| 4,848,374 | A * | 7/1989 | Chard et al. |
| 4,924,886 | A | 5/1990 | Litzinger |
| 4,955,397 | A | 9/1990 | Johnson et al. |
| 5,033,483 | A | 7/1991 | Clearman et al. |
| 5,101,838 | A | 4/1992 | Schwartz et al. |
| 5,105,834 | A * | 4/1992 | Saintsing et al. ............. 131/334 |
| 5,133,368 | A | 7/1992 | Neumann et al. |
| 5,327,915 | A | 7/1994 | Porenski et al. |
| 5,538,020 | A | 7/1996 | Farrier et al. |
| 6,102,036 | A | 8/2000 | Slutsky et al. |
| 6,772,756 | B2 | 8/2004 | Shayan |
| 6,929,004 | B1 | 8/2005 | Bonney et al. |
| 6,990,978 | B2 | 1/2006 | Shayan |
| 7,168,431 | B2 | 1/2007 | Li et al. |
| 2002/0017295 | A1 | 2/2002 | Weers et al. |
| 2004/0009128 | A1 | 1/2004 | Rabinowitz et al. |
| 2004/0034068 | A1 | 2/2004 | Warchol et al. |
| 2005/0053665 | A1 | 3/2005 | Ek et al. |
| 2005/0267120 | A1 | 12/2005 | Stenkamp et al. |
| 2006/0018840 | A1 | 1/2006 | Lechuga-Ballesteros et al. |
| 2006/0027243 | A1 | 2/2006 | Matsufuji et al. |
| 2007/0062548 | A1* | 3/2007 | Horstmann et al. .......... 131/270 |
| 2008/0241255 | A1 | 10/2008 | Rose et al. |
| 2013/0276804 | A1 | 10/2013 | Hon |

FOREIGN PATENT DOCUMENTS

| | | | |
|---|---|---|---|
| EP | 0354661 | A2 | 2/1990 |
| EP | 0520231 | | 12/1992 |
| EP | 0712584 | A2 | 5/1996 |
| GB | 248751 | A | 8/1926 |
| GB | 2199229 | A | 7/1988 |
| JP | H01104153 | A | 4/1989 |
| JP | H02190178 | A | 7/1990 |
| JP | 05-184675 | | 7/1993 |
| JP | 2005522206 | A | 7/2005 |
| JP | 2007512880 | A | 5/2007 |
| KR | 1019980008081 | | 4/1998 |
| RU | 2336001 | C2 | 10/2008 |
| WO | 9607336 | A2 | 3/1996 |
| WO | 2004091325 | A1 | 10/2004 |
| WO | 2006070288 | A2 | 7/2006 |
| WO | 2007042941 | A2 | 4/2007 |
| WO | 2008121610 | A1 | 10/2008 |

OTHER PUBLICATIONS

Hughes, T.W., et al., Nicotine Administration Ariel Smoking Devices, Produced during Minnesota Tobacco Litigation Case No. C1-04-8565, document dated Jul. 28, 1966.
Battelle Memorial Institute, Research Proposal regarding Project Ariel, Produced during Minnesota Tobacco Litigation Case No. C1-04-8565, document dated Jan. 3, 1962.
Glantz, Stanton A., et al., Chapter 3 Addiction and Cigarettes as Nicotine Delivery Devices, The Cigarette Papers, 1996, 74-77, University of California Press, Berkeley, USA, available in full at: http://publishing.cdlib.org/ucpressedbooks/view?docId=ft8489p25j;brand=eschol.
Reuter, B. [Title Unknown], The Legcy Tobacco Documents Library, May 24, 1999, pp. 1-12, Univeristy of California, San Francisco, available at http://legacy.library.uscf.edu/tid/mzf12a00.
International Search Report, issued on PCT/US2010/026614, mailed May 10, 2010.
International Preliminary Report on Patentability (IPRP) issued in PCT/US2010/026614, on Sep. 20, 2100, mailed Sep. 29, 2011.
Crouse, William E. et al., Nicotine Extraction Preliminary Study of Methods for High Nicotine Leaf Extraction, Lorillard Research Center Greensboro, Accession No. 795, pp. 89761275-89761285, Jun. 29, 1976.
Japanese Examination Report dated Sep. 5, 2014 issued in related JP Application No. 2012-500827, with English translation.
Japanese Office Action for Application No. 2012-500827 dated May 25, 2015, 18 pages. English translation included.

* cited by examiner

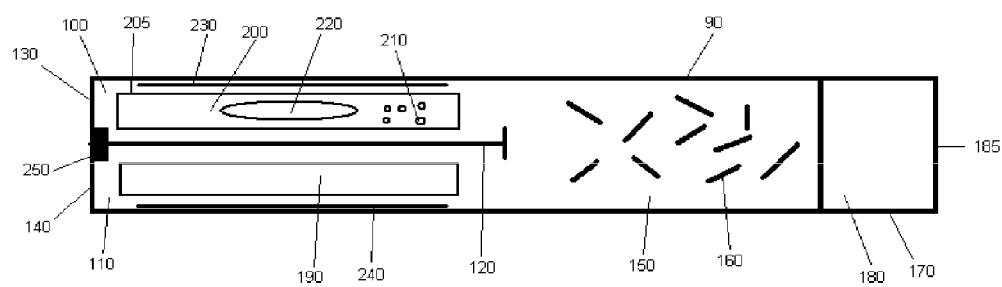
FIGURE 1
Figure 2A
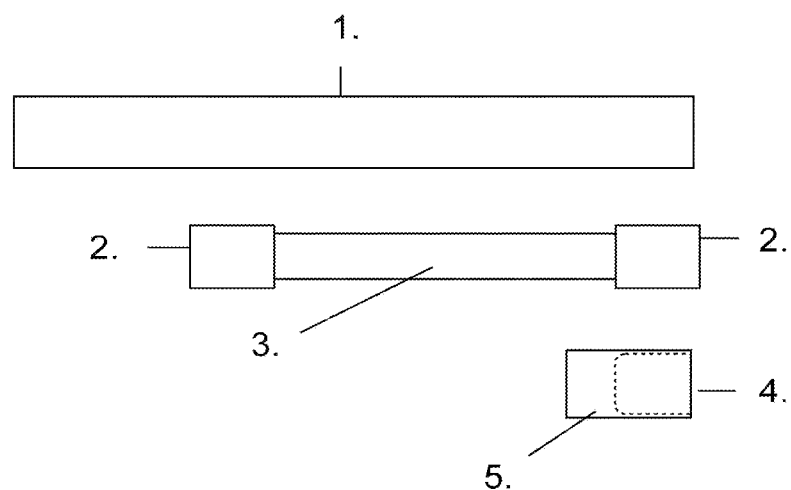

TOBACCO-BASED NICOTINE AEROSOL GENERATION SYSTEM

CROSS-REFERENCE TO RELATED APPLICATIONS

This application is a national stage application of PCT/US2010/026614 filed Mar. 9, 2010 claiming priority to U.S. Provisional 61/160,904 filed Mar. 17, 2009.

TECHNICAL FIELD

The invention relates to devices and methods for delivering nicotine and/or other alkaloids from tobacco, other plants and other natural sources. More particularly, the invention relates to devices and methods for delivering an aerosol of nicotine to a user's lungs without combustion of the nicotine source materials.

BACKGROUND ART

Pulmonary drug delivery systems have been used for decades to deliver medicaments for the treatment of respiratory disorders. The principle behind pulmonary drug delivery is aerosolization of drug compounds to be delivered to bronchioles and alveoli. Despite facing challenges like particle size optimization and degradation, a number of companies have developed technologies to deliver treatments for diabetes, migraine, osteoporosis and cancer.

Many preclinical and clinical studies have demonstrated that pulmonary delivery of medicaments is an efficient method for the treatment of both respiratory and systemic diseases. The many advantages of pulmonary delivery are well recognized and include rapid onset, patient self-administration, reduced side-effects, ease of delivery by inhalation, and the elimination of needles.

It has been reported that in order to deliver a powder directly into the lower respiratory regions the powder should generally have a particle size of less than 5 (im. Further, powders in the 5-10 um range have been found not to penetrate as deeply and instead tend to stimulate the upper respiratory tract regions.

Despite the foregoing medicinal applications, methods for the delivery of nicotine, other than by traditional combustion alternatives, have not significantly deviated from delivery via the traditional transdermal and oral routes to include pulmonary delivery via inhalation.

Nicotine can be more easily acquired and stored as tobacco (or other plant material) than in a purified form (e.g. nicotine base) and the nicotine therein is preserved in a more stable form. Also, use of tobacco as a source of nicotine facilitates delivery of the natural flavors therein. Moreover, other alkaloids naturally present in tobacco, such as nornicotine, may be delivered along with the nicotine.

Combustion to release nicotine, however, produces a complex mix of additional compounds and particles in the form of smoke. Near combustion heat or high temperature conditions (greater than 150 degrees C.) to release nicotine from tobacco requires significant energy and a heat delivery system sufficient in strength to provide the high heat required. The nicotine derived from the tobacco at near combustion temperatures represents a relatively minor portion of that available upon combustion.

Thus, there is a need for new methods to prepare aerosols for nicotine delivery utilizing tobacco or other plant products. The present disclosure describes in part a method for combining such nicotine with a compound for forming particles comprising the nicotine and/or other alkaloid(s) for delivery in a gaseous stream to generate an aerosol for pulmonary delivery.

DISCLOSURE OF INVENTION

Brief Summary of the Invention

In some embodiments, the disclosure relates to a method of delivering nicotine to a subject by inhalation, the method comprising the steps of:
  a) first placing a gaseous carrier in communication with a natural product nicotine source comprising a nicotine,
  b) second placing the gaseous carrier in communication with a source of a compound for forming particles comprising nicotine and/or other alkaloid(s), and
  c) third providing the gaseous carrier comprising the nicotine to a subject.

In some embodiments, the disclosure relates to a method of delivering nicotine to a subject by inhalation, the method comprising the steps of:
  a) first placing a gaseous carrier in communication with a source of a compound for forming particles comprising nicotine and/or other alkaloid(s),
  b) second placing the gaseous carrier in communication with a natural product nicotine source comprising a nicotine, and
  c) third providing the gaseous carrier comprising the nicotine to a subject.

In some embodiments, the disclosure relates to a method of delivering nicotine to a subject by inhalation, the method comprising the steps of:
  a) placing a first gaseous carrier in communication with a source of a compound for forming particles comprising nicotine and/or other alkaloid(s),
  b) placing a second gaseous carrier in communication with a natural product nicotine source comprising a nicotine,
  c) combining the first and second gaseous carriers to form nicotine particles in a combined gaseous carrier, and
  c) providing the combined gaseous carrier comprising the nicotine particles to a subject.

In some embodiments, the source of the compound for forming particles comprising nicotine and/or other alkaloid(s) comprises a plurality of internal areas comprising two or more precursor compounds.

In some embodiments, the compound for forming particles comprising nicotine and/or other alkaloid(s) comprises ammonium chloride and the two or more precursor compounds include ammonia and hydrogen chloride.

In some embodiments, the compound for forming particles comprising nicotine and/or other alkaloid(s) comprises an acid.

In some embodiments, the acid is an organic acid.

In some embodiments, the organic acid has a greater vapor pressure than nicotine base at a given temperature.

In some embodiments, the given temperature is 25, 30, 40, 45, 60, 70 or 100 degrees C.

In some embodiments, the acid is selected from the group consisting of 3-M ethyl-2-oxo valeric acid, Pyruvic acid, 2-Oxo valeric acid, 4-Methyl-2-oxovaleric acid, 3-Methyl-2-oxobutanoic acid, 2-Oxooctanoic acid and combinations thereof.

In some embodiments, the nicotine particles formed are less than 6 microns in Mass Median Aerodynamic Diameter.

In some embodiments, the particles are less than 1 micron in Mass Median Aerodynamic Diameter.

In some embodiments, at least some of the particles are between 0.5 and 5 microns in Mass Median Aerodynamic Diameter.

In some embodiments, a method comprises the step of increasing the temperature of the compound for forming particles comprising nicotine and/or other alkaloid(s), the source of the compound for forming particles comprising nicotine and/or other alkaloid(s), the nicotine and/or other alkaloid(s), the natural product nicotine source and/or the gaseous carrier.

In some embodiments, the temperature is increased to at least 30 or at least 60 degrees Celsius.

In some embodiments, the gaseous carrier comprises at least 10 micrograms of nicotine in a volume of gaseous carrier provided to the subject.

In some embodiments, the volume of gaseous carrier delivered to the subject is provided as a single volume.

In some embodiments, a method of tobacco product use cessation comprises a delivery to the subject of a therapeutically effective amount of nicotine to at least partially replace nicotine derived from a combustion tobacco product (e.g. cigarettes and cigars).

In some embodiments, a therapeutically effective amount of nicotine is provided to the subject.

In some embodiments, the disease is selected from the group consisting of nicotine addiction, obesity, Alzheimer's Disease, Parkinson's Disease, Ulcerative Colitis, Multiple Sclerosis and combinations thereof.

In some embodiments, a method of tobacco product substitution comprises delivering nicotine to a subject to substitute for nicotine derived from a combustion tobacco product (e.g. cigarettes and cigars).

In some embodiments, a method of tobacco product harm reduction comprises delivering nicotine to a subject to replace nicotine derived from a combustion tobacco product (e.g. cigarettes and cigars).

In some embodiments, a device is configured to be capable of carrying out the methods described herein.

In some embodiments, a device for delivering nicotine to a subject, comprises a housing, the housing comprising:
 a) an inlet and an outlet in communication with each other and adapted so that a gaseous carrier may pass into the housing through the inlet, through the housing and out of the housing through the outlet, the device comprising from inlet to outlet:
 b) a first internal area in communication with the inlet, the first internal area comprising either a source of the compound for forming particles comprising nicotine and/or other alkaloid(s) or a natural product nicotine source,
 c) a second internal area in communication with the first internal area, the second internal area comprising the other source listed for step b), and
 d) optionally, a third internal area in communication with the second internal area and the outlet.

In some embodiments, device for delivering nicotine to a subject, comprises a housing, the housing comprising:
 a) an inlet and an outlet in communication with each other and adapted so that a gaseous carrier may pass into the housing through the inlet, through the housing and out of the housing through the outlet, the device comprising from inlet to outlet:
 b) a first internal area in communication with the inlet, the first internal area comprising a source of the compound for forming particles comprising nicotine and/or other alkaloid(s),
 c) a second internal area in communication with the inlet, the second internal area comprising a natural product nicotine source, and
 d) optionally, a third internal area in communication with the first and second internal areas and the outlet.

In some embodiments, a partial vacuum at the outlet is capable of pulling the gaseous carrier through the inlet, the first compartment, the second compartment, the third compartment, when present, and then through the outlet.

In some embodiments, the source of the compound for forming particles comprising nicotine and/or other alkaloid(s) comprises an adsorption element with the compound for forming particles comprising nicotine and/or other alkaloid(s) adsorbed thereon.

In some embodiments, the adsorption element or elements comprises at least one of glass, aluminum, Polyethylene Terephthalate (PET), Polybutylene Terephthalate (PBT), Polytetrafluoroethylene (PTFE or TEFLON®), Expanded Polytetrafluoro ethylene (ePTFE) (ePTFE is described for example in U.S. Pat. No. 4,830,643), and BAREX®.

In some embodiments, a device comprises a first reservoir in communication with the source of the compound for forming particles comprising nicotine and/or other alkaloid(s), the first reservoir comprising the compound for forming particles comprising nicotine and/or other alkaloid(s).

In some embodiments, a device comprises a third internal area, the third internal area optionally comprising a gaseous carrier turbulence element and/or an additional source element.

In some embodiments, a device comprises an internal area element in communication with the outlet optionally comprising a purifying agent.

In some embodiments, purifying agent comprises activated charcoal.

In some embodiments, the third internal area element comprises a flavoring agent.

In some embodiments, the third internal area element comprises a medicament.

In some embodiments, medicament comprises nicotine.

In some embodiments, the housing simulates a tobacco smoking product.

In some embodiments, tobacco smoking product is a cigarette.

In some embodiments, the natural product nicotine source has been treated to increase the release of volatile nicotine and/or other alkaloid(s), from the natural product nicotine source, by one or more of the following:
 Minutizing the natural product nicotine source such as cutting, chopping or grinding.
 Raising the pH of the natural product nicotine source above neutral pH, such as above pH 8.0, above pH 9.0 or above pH 10.0.
 Mixing or homogenization of the natural product nicotine source to produce a liquefied suspension, optionally clarified to remove some to all visible particulate matter.
 Supplementing the natural product nicotine source with nicotine base.
 Treating the natural product nicotine source with enzymes or detergents to break down the cellulose contained therein in order to render the nicotine more available for release through volatilization or other means.
 Using molecular sieves or other desiccants to reduce the water content of the natural product nicotine source in order to increase the relative concentration of nicotine.
 Using high salt content solution (e.g. saturated NaCl solution or brine) to extract nicotine and other alkaloids. In particular embodiments, the high salt solution is contacted with the nicotine source (e.g. tobacco leaf) at >25 degrees C. and/or >pH 7.0 to increase the amount of nicotine extracted. See "Nicotine Extraction Preliminary Study of Methods for High Nicotine Leaf Extraction" http://tobaccodocuments.org/lor/89651655-1665.html. In other embodiments the nicotine and high salt content solution may be rendered basic and/or heated to concentrate the extracted nicotine into a separate phase for enhanced volatilization. The first treatment at >25 degrees C. and/or >pH 7.0 may be followed by the second treatment to render the resultant extract basic and/or heated.

In some embodiments, the temperature of one or more of a) the nicotine source, b) the source of the compound for forming particles comprising nicotine and/or other alkaloid(s) and/or c) the gaseous carrier, is below 150 degrees C., preferably below 100 degrees C. such as 25, 30, 40, 45, 60, 70 or 80±5 degrees C.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF DRAWINGS

For a more complete understanding of the present invention, reference is now made to the following descriptions taken in conjunction with the accompanying drawing, in which:

FIG. 1 is a plan view of an exemplary delivery device.

FIGS. 2A-C are a set of simplified schematics of the experimental device employed in some of the working examples; FIG. 2A, Components for Miniaturized Aerosol Device Used in Working Examples: 1. Teflon Tube (8 mm TD and 10 cm long), 2. Teflon Washer (7 mm OD), 3. Rolled Stainless Steel Screen (4 mm ID and 6 cm long), 4. Air-freshener plug, 5. Teflon Tube (7 mm OD); FIG. 2B, Components in the Assembled Device: 10. Outer housing for the pyruvic acid and tobacco sources, 20. Tobacco source, 30. Pyruvic acid source; FIG. 2C, Assembled, Sequential Design, Nicotine Delivery Device: 20. Moistened tobacco mixture packed in between rolled stainless steel screen and Teflon outer housing, 30. Pyruvic acid in air-freshener plug, 60. Gap between pyruvic acid source and tobacco source (2 cm), 40. Air inlet, 50. Outlet for tobacco aerosol.

FIGS. 3-7 are total ion chromatograms of various extracts.

DETAILED DESCRIPTION

"Particle" as used herein may refer to a liquid droplet, a solid particulate or a combination of both, such as a liquid droplet nucleated by a solid particulate.

"Therapeutically effective amount" as used herein may refer to a concentration or amount of nicotine which achieves a therapeutic effect in a subject, generally a human subject. The subject has an improvement in a disease or medically defined condition. The improvement is any alleviation or remediation of the symptoms associated with the disease. The improvement is an observable or measurable outcome of betterment. Thus, one of skill in the art realizes that a treatment may improve the disease condition, but may not be a complete cure for the disease. The therapeutic effect in some embodiments may include reduction or elimination of nicotine craving in a subject suffering nicotine addiction or in a subject experiencing nicotine use withdrawal symptoms.

The methods described herein relate to a surprising discovery regarding the dose of nicotine obtained from nicotine delivery devices utilizing tobacco as a source of nicotine. The inventors have unexpectedly identified methods for increasing the dose of nicotine delivered to a subject per unit weight of tobacco. The importance of this discovery lies in an improved ability to substitute for the nicotine delivery subjects experience while smoking cigarettes and similar tobacco combustion products. With improved nicotine delivery profiles, subjects applying the methods described herein will be provided with superior nicotine replacement therapy during attempts at smoking cessation, harm reduction and/or substitution. These discoveries may be further applied to other alkaloids from tobacco, as well as nicotine and other alkaloids from other plants and other natural sources.

In some embodiments, the methods involve the step of bringing a gaseous carrier in communication with a source of nicotine and/or other alkaloid(s). The gaseous carrier in these embodiments is then combined with a compound for forming particles comprising nicotine and/or other alkaloid(s) capable of improving particle formation of a size suitable for pulmonary delivery. In some embodiments, the compound for forming particles comprising nicotine and/or other alkaloid(s) is capable of reacting with nicotine base to form a salt. In particular embodiments, the compound for forming particles comprising nicotine and/or other alkaloid(s) is capable of reacting with nicotine base to form salt particles. In preferred embodiments, the particles are less than 6 micrometers, more preferably less than 1 micrometer, in Mass Median Aerodynamic Diameter. (For Mass Median Aerodynamic Diameter determinations, see Katz I M, Schroeter J D, Martonen T B, Factors affecting the deposition of aerosolized insulin, *Diabetes Technology & Therapeutics*, vol. 3 (3), 2001, pp 387-397, incorporated by reference for this teaching).

Gaseous Carrier and Source Thereof

Figure 2B:
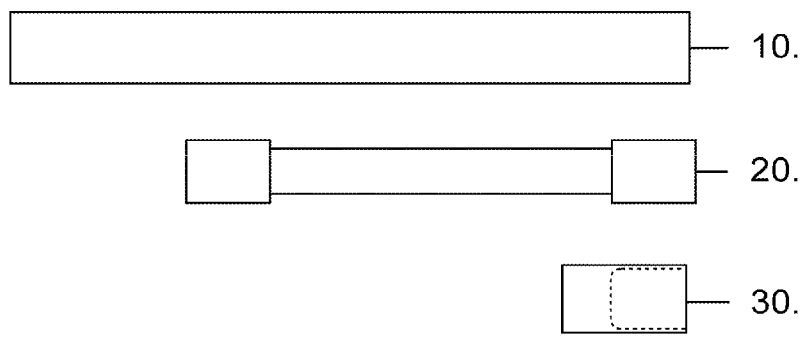

The gaseous carrier may be any gas capable of containing nicotine vapor, including nicotine base vapor, and the compound for forming particles comprising nicotine and/or other alkaloid(s). One of skill in the art will readily be able to select an appropriate gaseous carrier based on the intended use, form of nicotine and specific compounds for forming particles comprising nicotine and/or other alkaloid(s). In preferred embodiments, the gaseous carrier is substantially inert with regard to the form of nicotine and/or the compound for forming particles comprising nicotine and/or other alkaloid(s), at least for the time period contemplated for delivery to a subject. In some embodiments, the gaseous carrier is ambient air. In other embodiments the gaseous carrier is a substantially pure gas such as carbon dioxide or nitrogen gas, or a blend of such gases. In such embodiments, the gaseous carrier is supplied from a container designed to hold and deliver the gaseous carrier in a manner to effect the methods described herein. For example, in embodiments using metered dose inhaler devices, the gaseous carrier may comprise Hydrofluorocarbons, which include Hydrofluoroalkanes (HFAs) as propellants. In some of these embodiments, the HFAs are one or more of HFA 134a and HFA 227.

Compounds for Forming Particles Comprising Nicotine and/or Other Alkaloid(s)

Compounds for forming particles comprising nicotine and/or other alkaloid(s) are those compounds capable of increasing the total concentration of nicotine particles in either 1) a gaseous carrier loaded with a nicotine vapor or 2) a gaseous carrier loaded with the compound for forming particles comprising nicotine and/or other alkaloid(s) and then placed in communication with a nicotine source. Nicotine has a vapor pressure of 0.04 mm Hg at 25° C. Compounds for forming particles comprising nicotine and/or other alkaloid(s) having a vapor pressure greater than nicotine at a given temperature are preferred particularly if ambient temperatures are used. Non-limiting examples include inorganic acids such as hydrochloric, hydrobromic, or sulfuric acid, and organic acids including saturated and unsaturated aliphatic acids, saturated and unsaturated alicyclic acids, aromatic acids (including heterocyclic aromatic), polycarboxylic acids, hydroxy, alkoxy, keto, and oxo acids, thioacids, amino acids, and each of the preceding optionally substituted with one or more heteroatoms, including but not limited to halogens. In some embodiments, the compound for forming particles comprising nicotine and/or other alkaloid(s) is a carboxylic acid. In some of these embodiments, the carboxylic acid is in the class termed "2-Oxo acids." In some of these embodiments, the carboxylic acid is in the class of a-Keto acids known as "2-Keto acids." In some of these embodiments, the acid is selected from the group consisting of 3-Methyl-2-oxovaleric acid, Pyruvic acid, 2-Oxovaleric acid, 4-Methyl-2-oxovaleric acid, 3-Methyl-2-oxobutanoic acid, 2-Oxooctanoic acid and combinations thereof. In some embodiments, the compound for forming particles comprising nicotine and/or other alkaloid(s) forms solid particles, for example salt particles. Embodiments comprising such nicotine salt particles have the advantage of being neutralized such that the acrid, harsh flavor of nicotine base is avoided. In other embodiments, the compound for forming particles comprising nicotine and/or other alkaloid(s) forms a liquid droplet aerosol.

Alternatively, the compound for forming particles comprising nicotine and/or other alkaloid(s) forms a particulate aerosol, the particles of which may, for example, adsorb or absorb nicotine base. In particular embodiments, the particulate aerosol includes ammonium chloride salt particles. In embodiments comprising nicotine particle formation or nicotine adsorption/absorption onto particles the particles formed are preferably less than 6 microns, more preferably less than 5 microns or less than 1 micron in size.

Nicotine and/or Other Alkaloid(s) Sources

Any natural materials having nicotine and/or other alkaloid(s) content may be suitable for use as a nicotine source. Plant materials, in particular tobacco, are preferred. By way of example, the subsequent discussion will address nicotine from tobacco specifically.

In order to volatilize a sufficient amount of nicotine vapor from the tobacco, a number of parameters maybe adjusted, including: a) the temperature of the air stream entering the tobacco; b) the nicotine concentration of the tobacco; and/or c) the addition of other (preferably nonvolatile) alkaline substances (e.g., calcium oxide or calcium hydroxide or sodium hydroxide or sodium bicarbonate or potassium hydroxide or potassium carbonate) to tobacco (as in an aqueous solution) to promote the liberation of nicotine vapor; d) digestion of the plant with other agents, for example prior to alkalinization, may be performed to optimize nicotine yield.

Source of the Compound for Forming Particles Comprising Nicotine and/or Other Alkaloid(s)

In some embodiments of the methods, the gaseous carrier is provided pre-combined with the compound for forming particles comprising nicotine and/or other alkaloid(s). Other embodiments of the methods described herein include a step of loading a gaseous carrier with a compound for forming particles comprising nicotine and/or other alkaloid(s) prior to or concurrently with passage of the gaseous carrier over the nicotine source. Alternatively, the gaseous carrier may be first loaded with nicotine gas or vapor and then combined with the compound for forming particles comprising nicotine and/or other alkaloid(s). A sequential arrangement such as these has an advantage in terms of minimizing total air volume inhaled per puff, tending to maximize the nicotine concentration. Alternatively, a parallel arrangement may be used wherein the gaseous carrier is loaded with nicotine and compound for forming particles comprising nicotine and/or other alkaloid(s) separately and the two combined to form a gaseous carrier with nicotine particles. A parallel arrangement may avoid potential impediments (e.g. restrictive orifices) to the flow of aerosol particles through the device. A parallel arrangement also may in some embodiments mitigate the decline in nicotine yield over puffs that are sometimes observed with a sequential arrangement.

In embodiments encompassing a step of loading gaseous carrier (with or without nicotine) with a compound for forming particles comprising nicotine and/or other alkaloid(s), the compound for forming particles comprising nicotine and/or other alkaloid(s) is generally provided in the form of a source of the compound for forming particles comprising nicotine and/or other alkaloid(s). The gaseous carrier in these embodiments is generally brought into direct communication with the source such that the compound for forming particles comprising nicotine and/or other alkaloid(s) may enter the gaseous carrier from the source. In other embodiments the compound for forming particles comprising nicotine and/or other alkaloid(s) and nicotine are combined with a gaseous carrier separately and then the two combined to form nicotine particles in the gaseous carrier. In some embodiments, sources of the compound for forming particles comprising nicotine and/or other alkaloid(s) comprise source elements containing materials which adsorb or absorb the compound for forming particles comprising nicotine and/or other alkaloid(s). Source element materials will generally be inert with respect to the compound for forming particles comprising nicotine and/or other alkaloid(s). In some embodiments, the compound for forming particles comprising nicotine and/or other alkaloid(s) is an acid as described above. Non-limiting examples of adsorption element materials for such embodiments include glass, stainless steel, aluminum, PET, PBT, PTFE, ePTFE, and BAREX®. Non-limiting examples of absorption element materials for such embodiments include PE and PP.

A source of the compound for forming particles comprising nicotine and/or other alkaloid(s) may in some embodiments be, or be in communication with, a reservoir of the compound for forming particles comprising nicotine and/or other alkaloid(s). In some embodiments, the reservoir contains a volume of compound for forming particles comprising nicotine and/or other alkaloid(s) in liquid form with the liquid reservoir in communication with an adsorbing or absorbing source element. In other embodiments, the nicotine reservoir is or forms part of the source element. A non-limiting example of such a combination source and reservoir would be a material (e.g., PE or PP) saturated with a solution of a compound for forming particles comprising nicotine and/or other alkaloid(s). In particular embodiments, the reservoir provides sufficient solution to enable a delivery device to provide therapeutically effective doses of nicotine over a desired time frame. Non-limiting examples would be devices capable of delivering sufficient compound for forming particles comprising nicotine and/or other alkaloid(s) to enable delivery of 0-100 micrograms of nicotine per 35 cubic centimeter volume "puff of gaseous carrier for a desired number of puffs per day (e.g. 200) over a desired number of days (e.g. 1-7 days). In certain embodiments, the amount of nicotine delivered is between 10 and 110, 20 and 100, 50 and 100, or 40 and 60 micrograms of nicotine per 35 cubic centimeter volume "puff." Embodiments delivering 0 micrograms of nicotine are generally intended to be the end points of a gradual nicotine cessation program.

Temperature

In some embodiments of the methods, the method involves a step of increasing the temperature of one or more of the gaseous carrier, the tobacco or other plant product used as the nicotine and/or other alkaloid(s) source and the compound for forming particles comprising nicotine and/or other alkaloid(s). Such temperature control steps are generally used to regulate or to further enhance the amount of nicotine delivery. In some embodiments, the increase in temperature is used only if the nicotine levels delivered would generally be otherwise expected to drop below a desired minimum. In some embodiments this may be more than 20 micrograms, preferably more than 30 micrograms, and more preferably more than 40 micrograms of nicotine per 35 cc volume puff. For example, a common target delivery concentration is 40-50 micrograms nicotine per 35 cubic centimeter volume "puff as measured by a well known technique in the nicotine delivery field. See The FTC Cigarette Test Method for Determining Tar, Nicotine and Carbon Monoxide Yield of U.S. Cigarettes: Report of the NCI Ad Hoc Committee. Smoking and Tobacco Control Monograph #7. Dr. R. Shopland (Ed.). Darby, Pa.: Diane Publishing Co, 1996. In some embodiments, generally a lower temperature is used first with the temperature increasing over time to sustain a desired nicotine delivery concentration from a nicotine source. In other embodiments a constant temperature is maintained during use. In some embodiments, the temperature is elevated to a maximum of 100 degrees C., a maximum of 70 degrees C., a maximum of 80 degrees C., or the temperature is elevated to 80±5 degrees C. For example, the gaseous carrier or plant materials may be heated to 60 degrees C. to facilitate sustained nicotine release and delivery over multiple puffs at a desired nicotine concentration range (e.g. 20-50 micrograms per puff). Temperature control may in some embodiments be effected by a temperature control element. Such elements may be any known mechanism capable of achieving the desired target temperature for the gaseous carrier, the nicotine and/or the compound(s) for forming particles comprising nicotine and/or other alkaloid(s).

In particular embodiments, the same technique used to alkalinize the nicotine source (e.g. tobacco) with calcium oxide or calcium hydroxide or sodium hydroxide or sodium bicarbonate or potassium carbonate or potassium hydroxide, thereby increasing nicotine vapor formation, can also be used to heat the tobacco, further increasing the release of nicotine. For example, sodium hydroxide, when dissolved in water, liberates heat by an exothermic reaction.

The present disclosure provides methods for delivering nicotine and/or other alkaloid(s) from natural product nicotine sources such as tobacco at temperatures below 150 degrees C. These relatively low temperature embodiments in general have the advantage of reducing the complexity of the compounds released from the nicotine and/or other alkaloid(s) source. For example tobacco specific nitrosamines, such as 4-(methylnitrosamino)-1-(3-pyridyl)-1-butanone (NNK) and N'-nitrosonornicotine (NNN), are suspected carcinogens. See Hecht, S S; Hoffmann, D. Tobacco-specific nitrosamines, an important group of carcinogens in tobacco and tobacco smoke. Carcinogenesis. 1988; 9:875-884. These compounds have known boiling points above 150 degrees C. See Some Tobacco-specific N-Nitrosamines, IARC Monographs on the Evaluation of Carcinogenic Risks to Human, IARC Monographs, Volume 89 (2007); ISBN-13 9789283212898. Low temperature embodiments of the present invention operating below 150 degrees C., preferably below 100 degrees C. such as at 80±5 degrees C., are able for the first time to both produce sufficient nicotine vapor from tobacco to deliver therapeutically effective doses of nicotine per 35 cubic centimeter volume "puff while avoiding the increased volatilization of tobacco-specific nitrosamines that occurs above their boiling point (e.g. over 150 degrees C.). The importance of low temperature embodiments for reducing the number of compounds released is demonstrated in Experiment 10 below. A low temperature embodiment is tested for nitrogen compound release. The low temperature embodiment is compared to a typical commercial cigarette. As is shown and well know, cigarette smoke contains a complex mixture of nitrogen containing compounds such as the tobacco specific nitrosamines discussed above. The low temperature embodiment tested delivers nicotine while virtually eliminating release of the other nitrogen containing compounds seen in cigarette smoke. The importance of the low temperature is further demonstrated by comparison to the high temperature, noncombustion Accord system. Accord uses an electrical heater to elevate the temperature of tobacco to approximately 950 degrees F. (510 degrees C.). Holzman, D. "Safe Cigarette Alternatives? Industry Critics Say 'Not Yet'" Journal of the National Cancer Institute 1999 91(6): 502-504; doi:10.1093/jnci/91.6.502. This temperature is well below the combustion point for tobacco (approximately 1650° F.). As one would predict from the discussion above regarding tobacco specific nitrosamines, the Accord system still delivers a complex combination of nitrogenous compounds (although clearly less than that seen in tobacco smoke). Compared to the Accord system, the low temperature embodiments described herein represent a clear advance for reducing the complexity of co-released nitrogenous compounds in a tobacco based nicotine delivery system. These embodiments also have the advantage of reducing or eliminating side stream and/or second hand smoke.

Devices

The methods described herein are generally carried out using specially adapted delivery devices configured to carry out the methods described herein during device operation. One of skill in the art will be able to design and produce a variety of delivery devices using the foregoing guidance. The Inventors however provide herein a number of delivery device configurations to further illustrate the methods herein and their practical application by way of specific examples. The gaseous carrier delivered to a device user can include a therapeutically effective dose of nicotine for smoking cessation, harm reduction and/or substitution. Preferred delivery device embodiments are pulmonary delivery systems. Pulmonary delivery systems have the ability to deliver consistent doses with suitable particle-size and low particle-size variability, to the deep lung. Of the various non-invasive drug delivery technologies available, including nasal, transdermal, buccal, and needle-free injections, pulmonary delivery offers unique potential for precise dose titration, rapid absorption, and high bioavailability to deliver novel therapeutics and improve delivery of existing compounds.

MODES FOR CARRYING OUT THE INVENTION

Screening for a Suitable Experimental Design for Tobacco-Based Nicotine Aerosol Formation Several experimental designs were tested as described below to evaluate the generation of aerosol particles by allowing acid vapor to react instantly with base vapor.

Experiment #1: Pyruvic Acid Over Tobacco Powder Supplemented with Nicotine Base

Objective: The current experiments were designed to investigate the nicotine delivery in aerosol form when the pyruvic acid vapor passed over the tobacco mixture that was supplemented with nicotine base at 20% w/w of the dry tobacco weight Materials and Method:

Tobacco Mixture:

Tobacco from 2 Marlboro Lights cigarettes was triturated in mortar and pestle to produce a coarse powder of tobacco and was transferred into a side arm test tube. The weight of powder was 1.34 g and about 268 uL of nicotine base (20% with respect to dry powder weight) was added to the powder. The powder was mixed thoroughly (using spatula) with the added nicotine base. The volume of nicotine base was small when compared to the mass of powder, and thus the powder was not saturated with nicotine.

Pyruvic Acid:

About 2 mL of pyruvic acid was measured into a side arm glass test tube for each experiment and the air flow was introduced through a Pasteur pipette.

Testing Procedure:

Two identical side arm glass tubes (Tube A and B) were used for this experiment. Tube A had about 2 ml pyruvic acid and Tube B had a tobacco mixture (tobacco powder supplemented with 20% w/w nicotine base). The pyruvic acid vapors (from Tube A) were passed over tobacco mixture (Tube B) and the outlet from tube B was connected to a Cambridge filter to collect the reaction product upon pulling a volume of 35 cc air at 2 seconds duration (5 seconds interval) for 10 times (10 puffs) or 20 times (20 puffs) by using an automated syringe pump. The vapor formation in Tube A was enhanced by bubbling air through a glass pipette attached to it.

Results:

A dense cloud formation was observed upon passing the pyruvic acid vapor over the 20% w/w nicotine base supplemented tobacco powder mixture. The mean amounts of nicotine delivered in each 10 puffs of 35 cc volume are furnished in Table 1.

TABLE 1

Pyruvic acid vapor passed over 20% nicotine base supplemented tobacco powder at room temperature.

| Sample ID | Nicotine (μg)/puff |
|---|---|
| Pyruvic acid over 20% w/w nicotine supplemented tobacco powder -1 | 24.88 |
| Pyruvic acid over 20% w/w nicotine supplemented tobacco powder -2 | 4.92 |
| Pyruvic acid over 20% w/w nicotine supplemented tobacco powder -3 | 3.65 |
| Pyruvic acid over 20% w/w nicotine supplemented tobacco powder -4 | 4.01 |
| Pyruvic acid over 20% w/w nicotine supplemented tobacco powder -5 | 0.91 |
| Mean (in 50 puffs) Nicotine/puff = 7.67 | |
| About 2 ml of saturated solution of potassium carbonate added to the side arm glass tube that contained the tobacco powder and 268 μL nicotine base | |
| Pyruvic acid over 20% w/w nicotine supplemented alkaline tobacco mixture -1 | 14.13 |
| Pyruvic acid over 20% w/w nicotine supplemented alkaline tobacco mixture -2 | 12.20 |
| Pyruvic acid over 20% w/w nicotine supplemented alkaline tobacco mixture -3 | 12.93 |
| Pyruvic acid over 20% w/w nicotine supplemented alkaline tobacco mixture -4 | 12.26 |
| Pyruvic acid over 20% w/w nicotine supplemented alkaline tobacco mixture -5 | 21.41 |
| Mean (in 50 puffs) Nicotine/puff = 14.59 | |

Discussion:

The nicotine delivery in the first 10 puffs (mean of 24.88 μg/puff) with a dense visible cloud formation observed during the experiment suggests that using 20% w/w nicotine base supplemented tobacco powder is a successful strategy for obtaining the targeted (minimum of 10 μg/puff) delivery of nicotine in aerosol form. However, there was a dramatic fall off phenomenon observed from puff numbers 11 through 50 although there was a significant amount of nicotine in the test tube (268 mg of nicotine). The fall off might have been due to insufficient volume of nicotine base (liquid to powder ratio) to coat/moisten the whole amount of tobacco powder that led to improper distribution. In order to make the added amount of nicotine base available on the surface to form an aerosol with pyruvic acid vapor, we added about 2 mL of a saturated solution of potassium carbonate into the glass test tube that had the 20% w/w nicotine supplemented tobacco powder and collected 50 puffs. The nicotine delivery was constant without any dramatic fall off and also the mean nicotine delivery increased twofold (approximately 14 vs. 7 μg/puff). The data indicate that the tobacco powder should be moistened or soaked with an alkaline medium for sustained nicotine delivery with pyruvic acid.

Experiment #2: Pyruvic Acid Over Alkaline Mixture of Tobacco Supplemented with 20% Nicotine Base Objective:

The current experiments were designed to investigate the nicotine delivery in aerosol form when pyruvic acid vapor passed over the tobacco mixture that was supplemented with nicotine base at 20% w/w of the dried tobacco weight and alkalinized with saturated solution of lime (calcium oxide).

Materials and Method:

Tobacco Mixture:

About 1.5 g of tobacco from Marlboro Lights cigarettes was triturated and mixed with 300 uL of nicotine base (20% w/w of tobacco powder). After waiting for 10 minutes, the mixture was then transferred into a side arm glass test tube and treated with 5 mL of saturated solution of calcium oxide. The mixture was allowed to sit for 2 hours at room temperature and the pH was measured. The pH of the nicotine supplemented tobacco mixture was 11.91.

Pyruvic Acid:
About 2 mL of pyruvic acid was measured into a side arm glass test tube for each experiment and the air flow was introduced through a Pasteur pipette.

Testing Procedure:
The method described in the Experiment #1 was followed here except that the tube B contained 1.5 g powder of tobacco from cigarettes, 300 \iL of nicotine base and 5 mL of a saturated solution of calcium oxide.

Results:
Visible nicotine particle formation was seen and the mean amounts of nicotine delivered in each 10 puffs of 35 cc volume are furnished in Table 2.

TABLE 2

Pyruvic acid vapor passed over 20% nicotine base supplemented alkaline tobacco mixture at room temperature

| Sample ID | Nicotine (µg)/puff |
|---|---|
| Pyruvic acid over 20% w/w nicotine supplemented alkaline tobacco mixture -1 | 27.83 |
| Pyruvic acid over 20% w/w nicotine supplemented alkaline tobacco mixture -2 | 28.78 |
| Pyruvic acid over 20% w/w nicotine supplemented alkaline tobacco mixture -3 | 16.90 |
| Pyruvic acid over 20% w/w nicotine supplemented alkaline tobacco mixture -4 | 25.37 |
| Pyruvic acid over 20% w/w nicotine supplemented alkaline tobacco mixture -5 | 14.31 |
| Mean (in 50 puffs) Nicotine/puff = 22.64 | |

Discussion:
The data on the nicotine delivery clearly demonstrated that the nicotine delivery was enhanced when the 20% nicotine supplemented tobacco powder was soaked with a saturated solution of calcium oxide. The higher pH likely favored increased nicotine aerosol formation. In addition, the nicotine delivery was consistent with acceptable variability for at least 50 puffs.

Experiment #3: Pyruvic Acid Over Alkaline Mixtures of Tobacco Supplemented with 10% Nicotine Base Objective:
The reaction between water and sodium hydroxide pellets is exothermic and hence we hypothesized that the increased temperature due to exothermic reaction would enhance the nicotine delivery. Therefore, we aimed to take advantage of the heat generated (in situ) by the exothermic reaction to improve the nicotine aerosol delivery. As a preliminary experiment, we started with 10% w/w nicotine base added to tobacco powder.

Materials and Method:
Tobacco Mixture:
About 750 mg of tobacco from a Marlboro Lights cigarette was triturated to a coarse powder and mixed with 10% nicotine base (75 µL). About 2 gm of sodium hydroxide pellets was triturated (coarse powder) and mixed with the tobacco powder in a side arm glass test tube. Then, 3 mL of water was added to the side arm test tube and the temperature and pH were measured as 60° C. and 8.7, respectively.

Pyruvic Acid:
About 2 mL of pyruvic acid was measured into a side arm glass test tube for each experiment and the air flow was introduced through a Pasteur pipette.

Testing Procedure:
The method described in Experiment #1 was followed here except that the tube B contained 750 mg powdered tobacco from a cigarette, 75 uL of nicotine base and 3 mL of distilled water.

Results:
Visible particle formation was seen and the mean amount of nicotine delivered in each 10 puffs of 35 cc volume is furnished in Table 3.

TABLE 3

Pyruvic acid vapor passed over 10% nicotine base supplemented alkaline tobacco mixtures at room temperature.

| Sample ID | Nicotine (µg)/puff |
|---|---|
| Pyruvic acid over 10% w/w nicotine supplemented alkaline tobacco mixture -1 | 19.35 |
| Pyruvic acid over 10% w/w nicotine supplemented alkaline tobacco mixture -2 | 19.24 |
| Pyruvic acid over 10% w/w nicotine supplemented alkaline tobacco mixture -3 | 17.86 |
| Pyruvic acid over 10% w/w nicotine supplemented alkaline tobacco mixture -4 | 14.75 |
| Pyruvic acid over 10% w/w nicotine supplemented alkaline tobacco mixture -5 | 12.06 |
| Mean (in 50 puffs) Nicotine/puff = 16.65 | |

Discussion:
The data on the nicotine delivery demonstrated that the exothermic reaction enhanced the nicotine delivery, allowing a reduction in the nicotine supplementation of the tobacco from 20% to 10%. In other words, 10% nicotine supplementation of the tobacco in combination with heat (from exothermic reaction) yielded a nicotine delivery similar to that of 20% nicotine supplemented tobacco at room temperature. The current results are very encouraging as some species of tobacco have been reported to contain 8 to 10% of nicotine in the leaf. It should therefore be possible to obtain nicotine aerosol formation by using the leaves of natural tobacco in place of the 10% nicotine supplemented tobacco. The linear pattern of fall off in the current experiment can be correlated to the decreased temperature (temperature dependent delivery) of the tobacco mixture. This fall off could, we hypothesized, be compensated by maintaining the temperature throughout the experiment.

Experiment #4: Pyruvic Acid Over Heated Alkalinized Tobacco Supplemented with 10% Nicotine Base Objective:
We designed this experiment to investigate the effect of temperature on the nicotine delivery. In this experiment, a water bath served as a heating source to heat the tobacco mixture that had been supplemented with 10% w/w nicotine base.

Materials and Method:
Tobacco Mixture:
About 750 mg of tobacco from Marlboro Lights cigarettes was triturated to a coarse powder and mixed with 10% nicotine base (75 uL). About 2 gm of sodium hydroxide pellets was triturated (coarse powder) and mixed with the tobacco powder in a side arm glass test tube. Then, 3 mL of water was added to the side arm test tube and the temperature was measured to be 60° C. The pH of the nicotine supplemented tobacco mixture was 8.7.

Pyruvic Acid:
About 2 mL of pyruvic acid was measured into a side arm glass test tube for each experiment and the air flow was introduced through a Pasteur pipette.

Testing Procedure:
The method described in Experiment #1 was followed here except that the tube B contained 750 mg powdered tobacco from a cigarette, 75 \iL of nicotine base and 3 mL of distilled water and the side arm glass test tube was immersed into a water bath. The water bath temperature ranged from 88 to 96.2° C. for the experiment.

Results:

Visible nicotine particle formation was seen. The experimental results on the mean amounts of nicotine delivered in each 10 puffs of 35 cc volume are furnished in Table 4.

TABLE 4

Pyruvic acid vapor passed over heated 10% nicotine base supplemented tobacco mixture

| Sample ID | Nicotine Og)/puff | Temperature (° C.) |
|---|---|---|
| Pyruvic acid over heated 10% w/w nicotine supplemented alkaline tobacco mixture -1 | 88.52 | 88.5 |
| Pyruvic acid over heated 10% w/w nicotine supplemented alkaline tobacco mixture -2 | 65.69 | 88.8 |
| Pyruvic acid over heated 10% w/w nicotine supplemented alkaline tobacco mixture -3 | 71.79 | 90.0 |
| Pyruvic acid over heated 10% w/w nicotine supplemented alkaline tobacco mixture -4 | 64.15 | 92.8 |
| Pyruvic acid over heated 10% w/w nicotine supplemented alkaline tobacco mixture -5 | 54.88 | 96.2 |
| Mean (in 50 puffs) Nicotine/puff = 69.00 | | |

Discussion:

The data on the nicotine delivery exhibited that the heat enhanced the nicotine delivery dramatically. Although there is some variability in the nicotine delivery, there is no linear pattern of fall off. Hence, it is safe to conclude that application of heat to the nicotine supplemented tobacco enhanced the nicotine aerosol delivery significantly and also helped to diminish the fall off.

Experiment #5: Pyruvic Acid Over Heated Alkalinized Tobacco Supplemented with 5% Nicotine Base Objective:

We designed this experiment to investigate the effect of temperature on the nicotine delivery when pyruvic acid vapor passed over the tobacco that was supplemented with 5% w/w nicotine base.

Materials and Method:

Tobacco Mixture:

About 750 mg of tobacco from a Marlboro Lights cigarette was triturated to a coarse powder and mixed with 5% nicotine base (37.5 μL). About 2 gm of sodium hydroxide pellets were triturated (coarse powder) and mixed with the tobacco powder in a side arm glass test tube. Then, 3 mL of water was added to the side arm test tube and the temperature was measured to be 80° C. The pH of the nicotine supplemented tobacco mixture was 8.7.

Pyruvic Acid:

About 2 mL of pyruvic acid was measured into a side arm glass test tube for each experiment and the air flow was introduced through a Pasteur pipette.

Testing Procedure:

The method described in Experiment #1 was followed here except that the tube B contained 750 mg powdered tobacco from a cigarette, 37.5 μL of nicotine base and 3 mL of distilled water and the side arm glass test tube was immersed into a water bath. The water bath temperature ranged from 87.2 to 88.5° C. for the experiment.

Results:

Visible nicotine particle formation was seen. The experimental results on the mean amounts of nicotine delivered in each 10 puffs of 35 cc volume are furnished in Table 5.

TABLE 5

Pyruvic acid vapor passed over heated 5% nicotine base supplemented alkaline tobacco mixture.

| Sample ID | Nicotine (μg)/puff | Temperature (° C.) |
|---|---|---|
| Pyruvic acid over heated 5% w/w nicotine supplemented alkaline tobacco mixture -1 | 71.02 | 88.5 |
| Pyruvic acid over heated 5% w/w nicotine supplemented alkaline tobacco mixture -2 | 81.60 | 87.9 |
| Pyruvic acid over heated 5% w/w nicotine supplemented alkaline tobacco mixture -3 | 64.19 | 87.2 |
| Pyruvic acid over heated 5% w/w nicotine supplemented alkaline tobacco mixture -4 | 62.84 | 87.2 |
| Pyruvic acid over heated 5% w/w nicotine supplemented alkaline tobacco mixture -5 | 59.94 | 87.4 |
| Pyruvic acid over heated 5% w/w nicotine supplemented alkaline tobacco mixture -6 | 73.54 | 87.5 |
| Mean (in 60 puffs) Nicotine/puff = 68.86 | | |

Discussion:

The data on the nicotine delivery exhibited that the heat enhanced the nicotine delivery dramatically. The mean amount of nicotine aerosol delivery in the current experiment (with 5% nicotine base supplementation) is comparable to the 10% nicotine supplemented tobacco. Although there is some variability in the nicotine delivery, there is no linear pattern of fall off. Hence, application of heat to the nicotine supplemented tobacco has enhanced the nicotine aerosol delivery significantly and also helped to diminish the fall off. Furthermore, it is possible to achieve higher nicotine aerosol delivery even with 5% supplementation of nicotine base. This is an important result as many of the tobacco species have been reported to have about 5% nicotine in their leaves.

Experiment #6: Pyruvic Acid Over Heated Alkalinized Tobacco

Objective:

The previous experimental results (Experiment #5) have demonstrated that the nicotine aerosol delivery has been substantially enhanced even at 5% w/w nicotine base supplementation. Hence, we decided to conduct the current experiment using tobacco powder without any nicotine base supplementation to see if there is any significant nicotine aerosol formation.

Materials and Method:

Tobacco Mixture:

About 750 mg of tobacco from a Marlboro Lights cigarette was triturated to a coarse powder and mixed with about 2 gm of sodium hydroxide powder in a side arm glass test tube. Then, 3 mL of water was added to the tobacco and sodium hydroxide mixture (the temperature of the exothermic reaction between sodium hydroxide and water was measured as 80° C.). The pH of the tobacco mixture was 8.4.

Pyruvic Acid':

About 2 mL of pyruvic acid was measured into a side arm glass test tube for each experiment and the air flow was introduced through a Pasteur pipette.

Testing Procedure:

The method described in the Experiment #1 was followed here except that the tube B contained 750 mg powdered tobacco from cigarette and 2 g sodium hydroxide and 3 mL of distilled water; and the side arm glass test tube was immersed into a water bath. The water bath temperature ranged from 85.5 to 88.5° C. for the experiment.

Results:

Visible nicotine particle formation was observed. The experimental results on the mean amounts of nicotine delivered in each 10 puffs of 35 cc volume are furnished in Table 6.

TABLE 6

Pyruvic acid vapor passed over heated tobacco mixture at pH 8.4.

| Sample ID | Nicotine (p, g)/puff | Temperature (° C.) |
|---|---|---|
| Pyruvic acid over heated tobacco mixture -1 | 40.73 | 85.5 |
| Pyruvic acid over heated tobacco mixture -2 | 36.49 | 88.5 |
| Pyruvic acid over heated tobacco mixture -3 | 34.55 | 88.4 |
| Pyruvic acid over heated tobacco mixture -4 | 40.64 | 88.1 |
| Pyruvic acid over heated tobacco mixture -5 | 39.87 | 88.4 |
| Pyruvic acid over heated tobacco mixture -6 | 39.66 | 88.5 |
| Mean (in 60 puffs) Nicotine/puff = 38.66 | | |

Discussion:

The mean amount nicotine aerosol delivery in the current experiment (with no nicotine base supplementation) is very significant and there is no linear pattern of fall off in nicotine delivery over 60 puffs. It seems likely that the heat is serving to enhance nicotine evaporation and also helping to diminish the nicotine delivery fall off (which was observed in the room temperature experimental conditions).

Experiment #7: Pyruvic Acid over Heated Alkalinized Tobacco at pH 10

Objective:

We designed the current experiment based on the theory that the increased concentration of unprotonated (unionized) nicotine could be achieved in the tobacco mixture by increasing the pH to 10. Therefore, the unionized nicotine would facilitate the nicotine aerosol formation with pyruvic acid.

Materials and Method:

Tobacco Mixture:

About 750 mg of tobacco from a Marlboro Lights cigarette was triturated to a coarse powder and mixed with about 2 gm of sodium hydroxide powder in a side arm glass test tube. Then, 3 mL of water was added to the tobacco and sodium hydroxide mixture (the temperature of the exothermic reaction between sodium hydroxide and water was measured as 80° C.). The pH of the tobacco mixture was adjusted to 10 by addition of saturated solution of potassium carbonate and the final volume of the tobacco mixture increased to 11 mL.

Pyruvic Acid:

About 2 mL of pyruvic acid was measured into a side arm glass test tube for each experiment and the air flow was introduced through a Pasteur pipette.

Testing Procedure:

The method described in the Experiment #1 was followed here except that the tube B contained about 3 mL of the tobacco mixture (pH 10) and the side arm glass test tube was immersed into a hot water bath where the temperature ranged from 91.3 to 93.1° C.

Results:

Visible nicotine particle formation was seen. The experimental results on the mean amounts of nicotine delivered in each 10 puffs of 35 cc volume are furnished in Table 7.

TABLE 7

Pyruvic acid vapor passed over heated tobacco mixture at pH 10.

| Sample ID | Nicotine (μg)/puff | Temperature (° C.) |
|---|---|---|
| Pyruvic acid over heated tobacco mixture -1 | 57.08 | 92.4 |
| Pyruvic acid over heated tobacco mixture -2 | 66.42 | 93.1 |
| Pyruvic acid over heated tobacco mixture -3 | 65.37 | 93.1 |
| Pyruvic acid over heated tobacco mixture -4 | 65.42 | 92.5 |
| Pyruvic acid over heated tobacco mixture -5 | 54.33 | 91.3 |
| Mean (in 50 puffs) Nicotine/puff = 61.76 | | |

Discussion:

The nicotine delivery in the current experiment is significantly higher than the previous experiment (where the pH of the tobacco mixture was 8.4). It is also interesting to note that the nicotine deliveries were found to be substantial even when a portion of tobacco mixture was allowed to react with pyruvic acid vapor. Hence, the pH adjustment (preferably higher pH) in the tobacco mixture is critical to make the tobacco nicotine available in unprotonated or unionized form for the reaction with acid to yield higher nicotine delivery in the aerosol. It is plausible to conclude that the combination of heat and increased pH (using the sodium hydroxide and/or sodium bicarbonate or potassium carbonate or potassium hydroxide or calcium oxide or calcium hydroxide) in the tobacco mixture would be an appropriate approach to get enhanced nicotine aerosol formation with pyruvic acid.

Experiment #8: Investigation of Tobacco Aerosol Formation with Pyruvic Acid in a Miniaturized/Cigarette Sized Device (10 cm Long and 8 mm ID)

Objective:

The current experiment was conducted to design a cigarette-sized device. Hence, we attempted to translate the laboratory design into a size and shape appropriate for consumer use.

Materials and Method

Matrix Materials Used:

Air-freshener wick samples (X-40495 fiber from Porex Technologies) were used as a matrix in which pyruvic acid was loaded and a rolled version of stainless steel screen (70 S/Steel Mesh, TSI Filtration Technologies, Sanford, N.C. 27332) with a dimension of 4 mm ID and 6 cm long was used as a barrier between the moistened, alkalinized tobacco mixture and pyruvic acid air flow.

Tobacco Mixture Used:

About 750 mg of tobacco from a Marlboro Lights cigarette was triturated to a coarse powder and mixed with about 2 gm of sodium hydroxide coarse powder and moistened with 1.5 mL distilled water in a glass beaker.

Experimental Design:

A piece of air-freshener wick was loaded with 200 μL of pyruvic acid (pyruvic acid source element). The rolled stainless steel screen (stainless steel roll) with Teflon washers at both ends was inserted into an 8 mm ID and 10 cm long Teflon tube (outer housing). The moistened, alkalinized tobacco mixture was packed between the outer housing and stainless steel roll by making a 4 cm long longitudinal opening on the Teflon outer housing (tobacco source element). The longitudinal opening was closed by rolling Teflon tape and Parafilm tape such that there was no leak. The gap between the pyruvic acid source element and tobacco source element was 2 cm. The arrangement of the source elements was in such a way that a measured volume of air (35 cc at 2 sec duration and 5 second inter puff interval for 10 times) pulled by an automated syringe pump traveled first through the pyruvic acid source element and then through the tobacco source element to form an aerosol. The proximal end of the device was connected to an automated syringe pump containing a Cambridge filter to collect the aerosol products. For the elevated temperature (65-75° C.) experiment, the 6 cm long device (which had only a tobacco source element) was rolled with a thermal tape which was connected to a thermostat. The device was heated/equilibrated for 3 minutes prior to sampling.

Results:

The samples were analyzed for nicotine content and reported in Table 8 and Table 9.

TABLE 8

Nicotine delivery in a miniaturized device experiment at ambient temperature.

| Sample ID | Nicotine (µg/puff) |
|---|---|
| Pyruvic acid in air-freshener wick over tobacco source-1 | 7.16 |
| Pyruvic acid in air-freshener wick over tobacco source-2 | 6.57 |
| Pyruvic acid in air-freshener wick over tobacco source-3 | 6.41 |
| Pyruvic acid in air-freshener wick over tobacco source-4 | 6.43 |
| Mean nicotine (in 40puffs) | 6.64 |

TABLE 9

Nicotine delivery in a miniaturized device experiment at elevated temperature

| Sample ID | Nicotine (µg/puff) |
|---|---|
| Pyruvic acid in air-freshener wick over tobacco source-1 | 43.04 |
| Pyruvic acid in air-freshener wick over tobacco source-2 | 62.69 |
| Pyruvic acid in air-freshener wick over tobacco source-3 | 71.31 |
| Pyruvic acid in air-freshener wick over tobacco source-4 | 70.47 |
| Mean nicotine (in 40puffs) | 61.88 |

Discussion:

The data indicate that when both the acid and base were loaded onto a matrix, in this case, air-freshener for acid and rolled stainless steel screen for tobacco source, a comparable nicotine delivery was obtained as with the experimental apparatus used in Experiment 7. In addition, the elevated temperature (65-75° C.) condition dramatically increased the nicotine delivery (approximately 10 fold) when compared to the nicotine delivery at ambient condition.

Experiment #9: Particle Size Determination of the Aerosol Particles that were Generated by Nicotine in Alkalinized Tobacco Mixtures and Pyruvic Acid by Using Cascade Impactor About 2 mL of pyruvic acid was added into a side arm glass test tube (acid tube) and about 750 mg of tobacco powder from a Marlboro Lights cigarette and 2 gm of sodium hydroxide or calcium hydroxide or potassium hydroxide powder in another side arm glass test tube; and about 3 mL of water was added to the test tube (tobacco mixture tube). The acid tube was connected to the tobacco mixture tube in a sequential way where the acid vapor passed over the tobacco mixture. The tobacco mixture tube connected to a Cascade Impactor, which had 7 stages (as stage 3, 4, 5, 6, 7, 8 and filter). The outlet from the Cascade Impactor was connected to a Cambridge filter pad (backup filter) in order to collect the aerosol product upon pulling a volume of 35 cc air at 2 seconds duration (at 5 second intervals) for 100 times (100 puffs) using an automated syringe pump. Each stage of the Cascade Impactor was evaluated for nicotine content and calculated for Mass Median Aerodynamic Diameter (MMAD) of the aerosol particles and the results are furnished in Table 10.

TABLE 10

Particle size determination of tobacco aerosol

| Reactants | Stage number of Cascade Impactor | Nicotine ug/sample | Calculated Mass Median Aerodynamic Diameter (MMAD) of aerosol particles |
|---|---|---|---|
| Pyruvic acid alkalinized (with sodium hydroxide) tobacco mixture | 3 | 3.2 | 0.55 µm |
| | 4 | 3.0 | |
| | 5 | 3.0 | |
| | 6 | 2.8 | |
| | 7 | 3.1 | |
| | 8 | 5.0 | |
| | Filters | 24.1 | |
| Pyruvic acid alkalinized (with calcium hydroxide) tobacco mixture | 3 | 0.0 | 0.64 µm |
| | 4 | 0.0 | |
| | 5 | 0.0 | |
| | 6 | 0.0 | |
| | 7 | 3.7 | |
| | 8 | 31.0 | |
| | Filters | 54.3 | |
| Pyruvic acid alkalinized (with potassium hydroxide) tobacco mixture | 3 | 0.0 | 0.51 µm |
| | 4 | 0.0 | |
| | 5 | 0.0 | |
| | 6 | 0.0 | |
| | 7 | 0.0 | |
| | 8 | 4.4 | |
| | Filters | 45.7 | |

Experiment #10: Qualitative Investigation of Chemical Compounds (Nitrogen Containing Compounds) in the Samples Obtained from Tobacco Aerosol, Ruyan E-Cigarette, Ruyan Cigar, Accord Cigarette and Marlboro Lights Cigarette Objective:

The current experiment was a preliminary attempt to identify the number of chemical compounds (nitrogen containing compounds) in the tobacco aerosol when compared with some commercially available nicotine delivery systems or devices.

Materials and Method:

Collection of Tobacco Aerosol:

Pyruvic acid vapor from about 2 mL of pyruvic acid in a side arm glass test tube (acid tube) was passed over another side arm test tube that contained about 750 mg of tobacco powder from a Marlboro Lights cigarette, 2 gm of sodium hydroxide and 3 mL of water. The latter tube was connected to an automated syringe pump through a Cambridge filter to collect 10 puffs (35 cc, 2 seconds duration and 5 seconds inter puff interval). The Cambridge filter was soaked in 5 mL of methanol and extracted to obtain the tobacco aerosol extract.

Collection of Samples from Commercial Products:

Accord cigarette was inserted into an Accord heating system and the filter side was connected to an automated syringe pump. Likewise, the mouth piece of Ruyan e-cigarette, Ruyan cigar and filter of a Marlboro Lights cigarette (after ignition) was connected to the automated syringe pump and 10 puffs were collected (35 cc, 2 second duration and 5 second inter puff interval) in a Cambridge filter from each device. The Cambridge filter was soaked in 5 mL of methanol and extracted to obtain Accord cigarette extract, Ruyan e-cigarette extract, Ruyan cigar extract and Marlboro Cigarette extract.

Instrumentation:

About 1 uL of the Tobacco aerosol extract, Ruyan e-cigarette extract, Ruyan cigar extract, Accord cigarette extract and Marlboro cigarette extract was injected individually into a Gas Chromatography system (Agilent GC-HP6890 Series with NPD). The parameters for all the sample injections were identical.

Results:

The total ion chromatograms (TIC) of the tested samples (Tobacco aerosol extract, Ruyan e-cigarette extract, Ruyan cigar extract, Accord cigarette extract and Marlboro cigarette extract) are presented in the following pictures.

Figure 3:
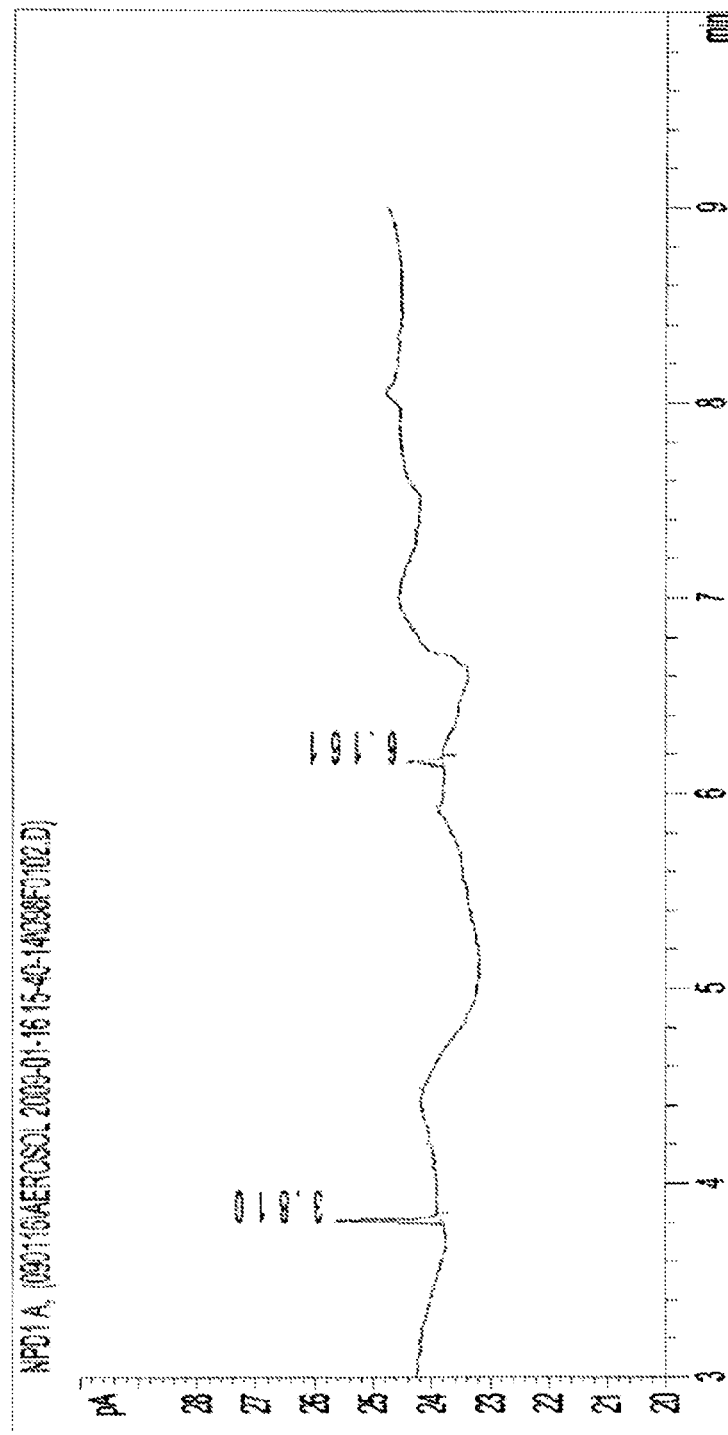

FIG. 3 shows a Total Ion Chromatogram of Tobacco Aerosol Extract.

Figure 4:
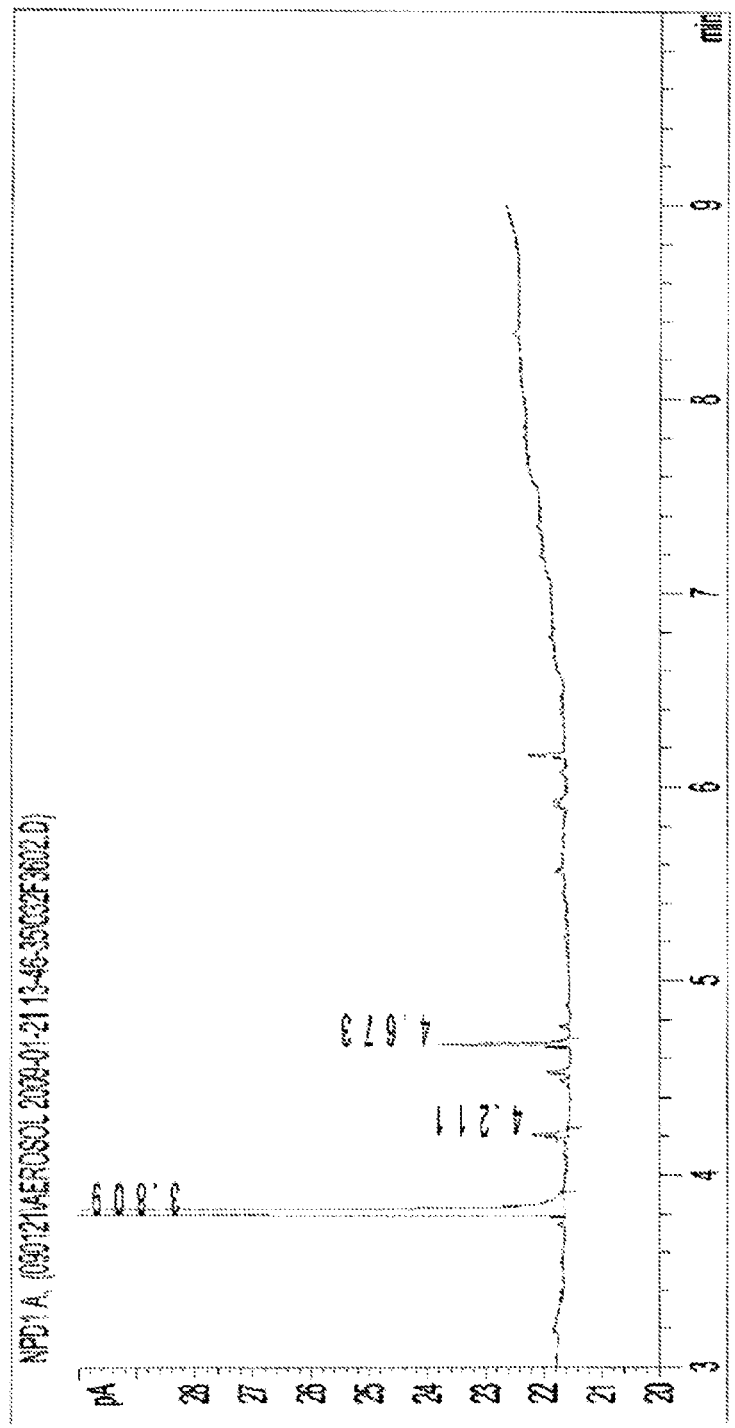

FIG. 4 shows a Total Ion Chromatogram of Ruyan E-Cigarette Extract.

Figure 5:
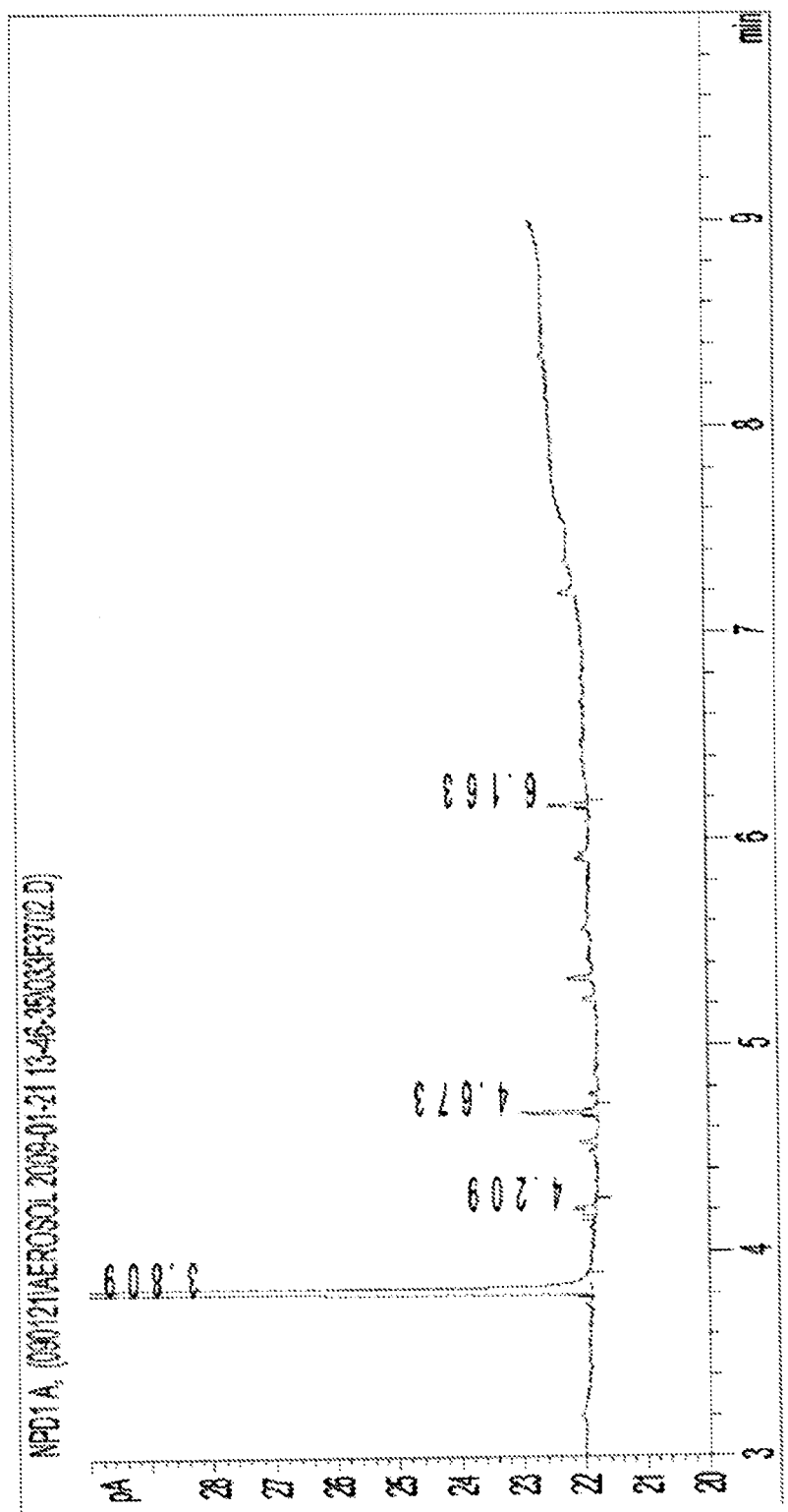

FIG. 5 shows a Total Ion Chromatogram of Ruyan Cigar Extract.

Figure 6:
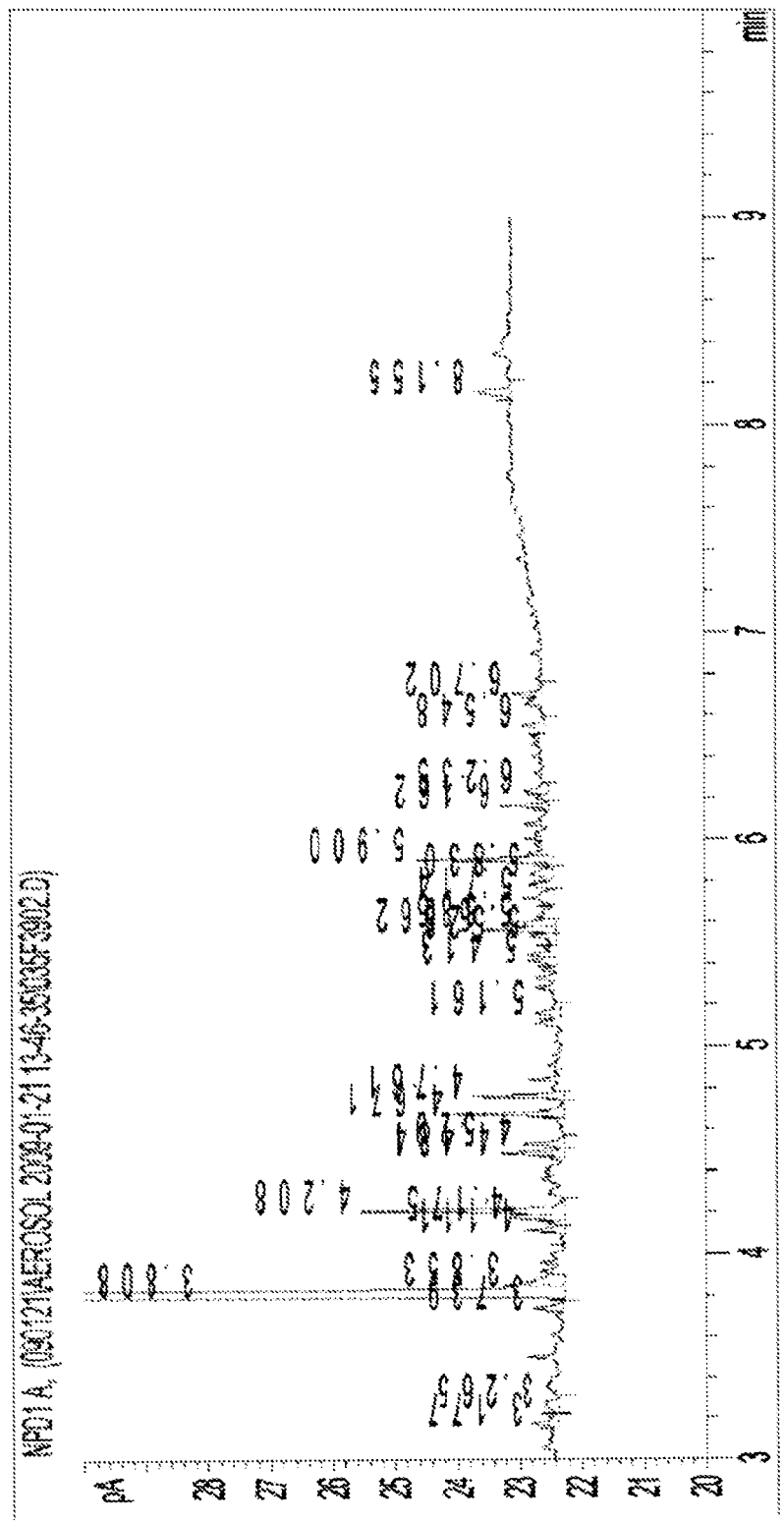

FIG. 6 shows a Total Ion Chromatogram of Accord Cigarette Extract.

Figure 7:
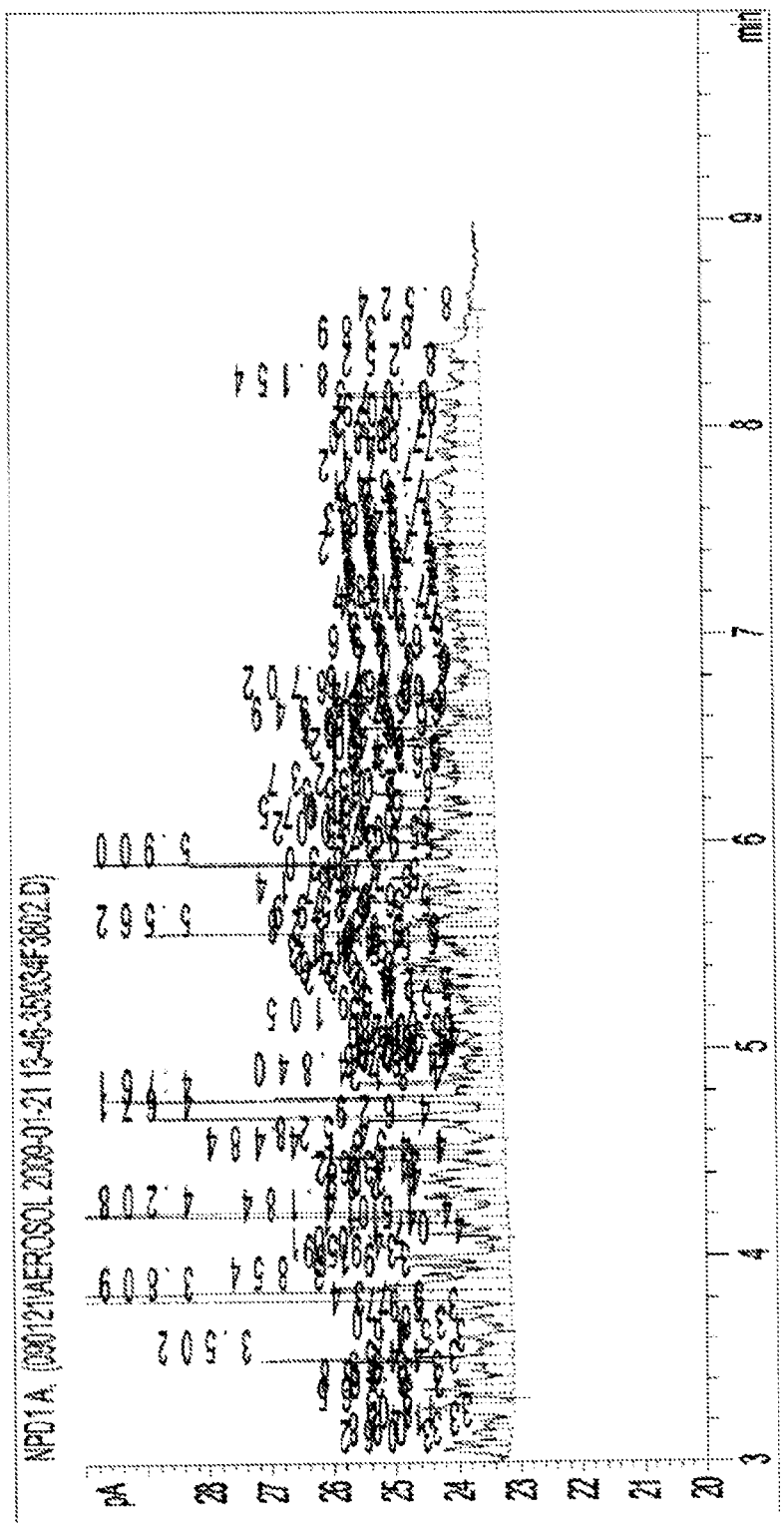

FIG. 7 shows a Total Ion Chromatogram of Marlboro Cigarette Extract.

Discussion:

The graphical illustration (x-axis is retention time and y-axis is the response factor) of the total ion chromatogram (TIC) of tobacco aerosol extract has clearly demonstrated that the extract has two peaks for nitrogen containing compounds. While we knew that the peak at retention time 3.8 is for nicotine, the substance responsible for the other peak at retention time 6.16 is not identified. Based on the qualitative TICs, it is very clear that the tobacco aerosol extract is the purest one while the Marlboro cigarette extract is the most complex mixture of nitrogen containing compounds. Furthermore, certain nitrogen containing compounds have been linked to the carcinogenic effects in smokers; the tobacco aerosol will avoid the delivery of these carcinogenic compounds. From these experimental results, it can be concluded that the tobacco aerosol is a superior nicotine delivery system with a negligible amount of other nitrogen containing chemicals when compared to the prior art.

Exemplary Devices Adapted for Use with the Methods Herein

Delivery devices of some embodiments comprise a housing which simulates a tobacco smoking article. The housing may simulate the size, shape, and/or configuration of any article used for smoking tobacco articles. Non-limiting examples of smoking articles according to the present invention include cigarettes, cigars, cigarillos and pipes.

Delivery devices of some embodiments comprise a housing which simulates a pharmaceutical inhalation device. The housing may simulate the size, shape, and/or configuration of any pharmaceutical device used for inhalation. Non-limiting examples of pharmaceutical inhalation devices according to the present invention include, metered dose inhalers, pressurized metered dose inhalers, dry powder inhalers, nebulizers and liquid based inhalers.

Exemplary Devices

FIG. 1 is a simplified schematic of a device for use in a parallel particle formation process. The device exterior wall 90 may be a flexible, insulating material such as reflective aluminum foil and/or deformable material defining two concentric walls with an air barrier or vacuum in between. Compartments 100 and 110 contain the natural product nicotine source and the source of the compound for forming particles comprising nicotine and/or other alkaloid(s), respectively. These are separated by a dividing wall 120. The gaseous carrier enters compartments 100 and 110 through apertures 130 and 140, respectively, picks up nicotine vapor and particle forming compound, and carries these into mixing chamber 150 where optional baffles 160 create turbulence for mixing. The resulting nicotine particles then pass through optional compartment 170 which may have a filter 180 for, e.g., removing unreacted compound for forming particles comprising nicotine and/or other alkaloid(s). The particles comprising nicotine then are carried by the gaseous carrier out aperture 185. Element 190 is the source of compound for forming particles comprising nicotine. The source element 190 may be for example an cPTFE fiber plug saturated with pyruvic acid. The nicotine source 200 is in this embodiment a plug of finely cut or ground tobacco held together by a flexible, mesh encasement 205 having 3-5 micrometer pores. Within the tobacco are powdered alkalinization compounds 210 such a NaOH in this example. Also encased with nicotine source 200 is an ampoule 220 of water or an aqueous solution such as water saturated with NaCl. The ampoule 220 is adapted to rupture upon application of pressure to deform exterior wall 90 and compress encasement 205. This releases the water which dissolves the alkalinization compound NaOH 210. This reaction is generally exothermic and thus contributes heat to further increase the release of nicotine. Using the chemical reaction as the heating source will generally be in embodiments where device exterior wall 90 is a flexible, insulating material. Temperature may also be optionally controlled by flexible heating element sheets 230 and 240 lining compartments 100 and 110 and/or a heating element integral to dividing wall 120. Heating elements will generally be powered by a battery 250. For long term storage (e.g. >90 days), the device may be adapted to be sealed and or resealable at apertures 130, 140 and 185. In alternative configurations, compartments 100 and 110 may be arranged in linear sequence such that a gaseous carrier passes through one then the next in succession before entering mixing chamber 150.

Figure 2C:
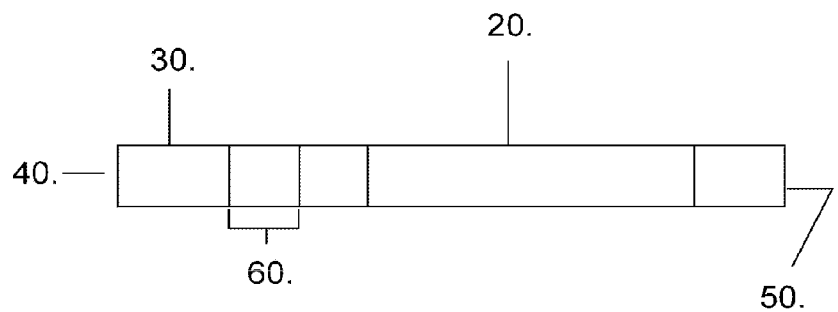

FIGS. 2A-C shows an exemplary device having a sequential configuration with the source of the compound for forming particles comprising nicotine (pyruvic acid) then the natural product nicotine source (tobacco). The details of this device are disclosed in the discussion of Experiment #8 above and in the figure texts.

INDUSTRIAL APPLICABILITY

The methods and devices herein are useful for the therapeutic delivery of nicotine for smoking cessation, harm reduction and/or substitution. In addition, the devices and methods herein are useful as an alternative, general nicotine delivery system in place of tobacco combustion or high temperature (over 150 degrees C.) products.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

All references and other information cited to, or otherwise identified herein, are hereby incorporated by reference in their entireties as if each had been separately so incorporated.

The invention claimed is:

1. A device for delivering nicotine to a subject, the device comprising a noncombustible housing, the noncombustible housing comprising:
    a) an inlet and an outlet in communication with each other and adapted so that a gaseous carrier may pass into the housing through the inlet, through the housing and out of the housing through the outlet, the device comprising from inlet to outlet;
    b) a first internal area in communication with the inlet, the first internal area comprising either a source of a compound for forming particles comprising nicotine, or a source of a natural product nicotine comprising powdered tobacco; and
    c) a second internal area in communication with the first internal area, the second internal area comprising the source not selected for step b.

2. The device according to claim 1, wherein a third internal area is in communication with the second internal area and the outlet.

3. The device according to claim 1 wherein the first internal area comprises the source of a compound for forming particles comprising nicotine and the second internal area comprises the source of a natural product nicotine comprising powdered tobacco.

4. A device for delivering nicotine to a subject, the device comprising a noncombustible housing, the noncombustible housing comprising:
    a) a first inlet, a second inlet and an outlet in communication with each other and adapted so that a first gaseous carrier may pass into the noncombustible housing through the first inlet, through the noncombustible housing and out of the noncombustible housing through the outlet, and a second gaseous carrier may pass into the noncombustible housing through the second inlet, through the noncombustible housing and out of the noncombustible housing through the outlet, the device comprising:
    b) a first internal area in communication with the first inlet, the first internal area comprising a source of a compound for forming particles comprising nicotine;
    c) a second internal area in communication with the second inlet, the second internal area comprising a source of a natural product nicotine comprising powdered tobacco; and
    d) a third internal area in communication with the first and second internal areas and the outlet.

5. The device according to claim 1, wherein the source of a compound for forming particles comprising nicotine comprises an adsorption element with the compound for forming particles comprising nicotine adsorbed thereon.

6. The device according to claim 1, wherein the natural product nicotine source comprises powdered tobacco and an alkaline substance.

7. The device according to claim 6, wherein the alkaline substance is selected from the group consisting of calcium oxide, calcium hydroxide, sodium hydroxide, sodium bicarbonate, potassium hydroxide and potassium carbonate.

8. The device according to claim 1, further comprising a first reservoir in communication with the source of a compound for forming particles comprising nicotine, the first reservoir comprising the compound for forming particles comprising nicotine and/or other alkaloid(s).

9. The device according to claim 1, wherein the source of a compound for forming particles comprising nicotine and/or other alkaloid(s) comprises a plurality of internal areas comprising two or more precursor compounds.

10. The device according to claim 9, wherein the compound for forming particles comprising nicotine and/or other alkaloid(s) comprises ammonium chloride and the two or more precursor compounds include ammonia and hydrogen chloride.

11. The device according to claim 1, wherein the compound for forming particles comprising nicotine comprises an acid.

12. The device according to claim 11, wherein the acid is an organic acid.

13. The device according to claim 12, wherein the acid is a 2-Keto acid.

14. The device according to claim 13, wherein the acid is selected from the group consisting of 3-Methyl-2-oxovaleric acid, Pyruvic acid, 2-Oxovaleric acid, 4-Methyl-2-oxo valeric acid, 3-Methyl-2-oxobutanoic acid, 2-Oxooctanoic acid and combinations thereof.

15. The device according to claim 1, wherein the housing simulates a tobacco product.

16. The device according to claim 1, further comprising a third internal area, the third internal area comprising a gaseous carrier turbulence element and/or an additional source element.

17. The device according to claim 1, further comprising an internal area element in communication with the outlet wherein the element comprises a purifying agent.

18. The device according to claim 16, wherein the third internal area element comprises a flavoring agent.

19. The device according to claim 1, wherein the natural source nicotine comprising powdered tobacco is heated.

20. The device according to claim 1, wherein the temperature of at least: a) the natural product nicotine comprising powdered tobacco, b) the source of a compound for forming particles comprising nicotine, and c) the gaseous carrier is below 150 degrees C. when the particles comprising nicotine are formed.

21. The device according to claim 1, wherein the temperature of at least: a) the natural product nicotine comprising powdered tobacco, b) the source of a compound for forming particles comprising nicotine, and c) the gaseous carrier is below 100 degrees C. when the particles comprising nicotine are formed.

22. The device according to claim 1, wherein the source of a natural product nicotine comprising powdered tobacco has been treated to increase the release of volatile nicotine, from the source of a natural product nicotine, by one or more of the following:
    a) Minutizing the natural product nicotine source such as cutting, chopping or grinding;
    b) Raising the pH of the natural product nicotine source above neutral pH,
    c) Mixing or homogenization of the natural product nicotine source to produce a liquefied suspension, optionally clarified to remove some to all visible particulate matter;
    d) Supplementing the natural product nicotine source with nicotine base;
    e) Treating the natural product nicotine source with enzymes or detergents to break down the cellulose contained therein in order to render the nicotine more available for release through volatilization or other means;
    f) Using molecular sieves or other desiccants to reduce the water content of the natural product nicotine source in order to increase the relative concentration of nicotine; and
    g) Using high salt content solution to extract nicotine.

23. A method of delivering nicotine to a subject by inhalation, the method comprising the steps of:
   a) first placing a gaseous carrier in communication with either a source of a compound for forming particles comprising nicotine, or a source of a natural product nicotine source comprising powdered tobacco;
   b) second placing the gaseous carrier in communication with the source not selected for step a) to form particles comprising nicotine; and
   c) third providing the gaseous carrier comprising the particles comprising nicotine to a subject, wherein first and second step is performed at a temperature below 150 degrees centigrade.

24. The method according to claim 23, further comprising the steps of:
   a) first placing the gaseous carrier in communication with the compound for forming particles comprising a source of nicotine to form a loaded gaseous carrier;
   b) second placing the loaded gaseous carrier in communication with the natural product nicotine source comprising powdered tobacco to form the particles comprising nicotine; and
   c) third providing the gaseous carrier comprising the particles comprising nicotine to a subject.

25. A method of delivering nicotine to a subject by inhalation, the method comprising the steps of:
   a) placing a first gaseous carrier in communication with a source of a compound for forming particles comprising nicotine;
   b) placing a second gaseous carrier in communication with a source of natural product nicotine comprising powdered tobacco;
   c) combining the first and second gaseous carriers to form nicotine particles in a combined gaseous carrier; and
   d) providing the combined gaseous carrier comprising the nicotine particles to a subject wherein the placing steps and the combining step are performed at a temperature below 100 degrees centigrade.

26. The method according to claim 23, wherein the nicotine particles formed are less than 6 microns in Mass Median Aerodynamic Diameter.

27. The method according to claim 23, further comprising the step of increasing the temperature of at least one or more of a) the source of natural product nicotine comprising powdered tobacco; b) the source of a compound for forming particles comprising nicotine; and c) the gaseous carrier.

28. The method according to claim 23, wherein the natural product nicotine source comprising powdered tobacco has been treated to increase the release of nicotine from the natural product source, by one or more of the following:
   a) Minutizing the natural product nicotine source such as cutting, chopping or grinding;
   b) Raising the pH of the natural product nicotine source above neutral pH;
   c) Mixing or homogenization of the natural product nicotine source to produce a liquefied suspension, optionally clarified to remove some to all visible particulate matter;
   d) Supplementing the natural product nicotine source with nicotine base;
   e) Treating the natural product nicotine source with enzymes or detergents to break down the cellulose contained therein in order to render the nicotine more available for release through volatilization or other means;
   f) Using molecular sieves or other desiccants to reduce the water content of the natural product nicotine source in order to increase the relative concentration of nicotine; and
   g) Using high salt content solution to extract nicotine.

29. The method according to claim 23, comprising supplementing the natural product nicotine source with nicotine base.

30. The method of tobacco product substitution comprising delivering nicotine to a subject by a method according to claim 23.

* * * * *